(12) United States Patent  (10) Patent No.: US 8,979,801 B2
Lamson et al.  (45) Date of Patent: Mar. 17, 2015

(54) MICROCATHETER DEVICES AND METHODS FOR TARGETED SUBSTANCE DELIVERY

(75) Inventors: Theodore Lamson, Pleasanton, CA (US); Patrick Macaulay, Windsor, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 856 days.

(21) Appl. No.: 11/279,771

(22) Filed: Apr. 14, 2006

(65) Prior Publication Data

US 2006/0173440 A1 Aug. 3, 2006

Related U.S. Application Data

(63) Continuation-in-part of application No. 10/458,153, filed on Jun. 10, 2003, now Pat. No. 7,606,615, which is a continuation of application No. 09/766,502, filed on Jan. 17, 2001, now Pat. No. 6,602,241.

(51) Int. Cl.
  *A61M 5/178* (2006.01)
  *A61M 25/00* (2006.01)
  *A61B 18/14* (2006.01)
  *A61B 17/00* (2006.01)
  *A61B 18/00* (2006.01)

(52) U.S. Cl.
  CPC ......... *A61M 25/007* (2013.01); *A61M 25/0068* (2013.01); *A61M 25/0069* (2013.01); *A61M 25/0084* (2013.01); *A61B 18/1477* (2013.01); *A61B 2017/00247* (2013.01); *A61B 2018/00392* (2013.01); *A61B 2018/1425* (2013.01); *A61M 25/0082* (2013.01); *A61M 2025/0042* (2013.01); *A61M 2025/0092* (2013.01); *A61M 2025/0096* (2013.01)
  USPC .................................................. 604/164.01

(58) Field of Classification Search
  USPC .......................... 604/164.01, 22, 529; 600/439
  See application file for complete search history.

(56) References Cited

U.S. PATENT DOCUMENTS

| | | | | |
|---|---|---|---|---|
| 5,445,142 | A * | 8/1995 | Hassler, Jr. | 600/105 |
| 5,951,547 | A * | 9/1999 | Gough et al. | 606/41 |
| 6,206,847 | B1 * | 3/2001 | Edwards et al. | 604/22 |
| 6,544,230 | B1 * | 4/2003 | Flaherty et al. | 604/164.12 |
| 6,613,026 | B1 * | 9/2003 | Palasis et al. | 604/272 |
| 6,685,648 | B2 * | 2/2004 | Flaherty et al. | 600/464 |
| 6,719,725 | B2 * | 4/2004 | Milo et al. | 604/164.01 |
| 6,726,677 | B1 * | 4/2004 | Flaherty et al. | 604/528 |
| 2001/0023349 | A1 * | 9/2001 | VanTassel et al. | 606/53 |
| 2003/0236542 | A1 * | 12/2003 | Makower | 606/167 |
| 2007/0156093 | A1 * | 7/2007 | Woehr | 604/164.08 |
| 2009/0228092 | A1 * | 9/2009 | Raeder-Devens et al. | 623/1.11 |

* cited by examiner

*Primary Examiner* — Jason Flick

(57) ABSTRACT

Delivery catheters useable to deliver substances, articles or devices to target locations within the bodies of human or animal subjects. The delivery catheter generally comprises a catheter having a tissue penetrating distal tip member on the distal end and one or more delivery aperture(s) whereby a substance, article or device may be delivered through the lumen of the catheter body and out of the delivery aperture(s). In some applications, the substance delivery catheter is used in combination with a transluminal tissue penetrating catheter having a penetrator that is advanced to a first location. The delivery catheter is then advanced through (or over) the penetrator, through intervening tissue, to a desired target location.

12 Claims, 5 Drawing Sheets

MICROCATHETER DEVICES AND METHODS FOR TARGETED SUBSTANCE DELIVERY

RELATED APPLICATION

This patent application is a continuation-in-part of copending U.S. patent application Ser. No. 10/458,153 entitled "Methods and Apparatus for Acute or Chronic Delivery of Substances or Apparatus to Extravascular Treatment Sites" filed Jun. 10, 2003, which is a continuation of U.S. patent application Ser. No. 09/766,502 filed Jan. 17, 2001 now issued as U.S. Pat. No. 6,602,241, the entire disclosure of each such related application being expressly incorporated herein by reference.

FIELD OF THE INVENTION

The present invention relates generally to methods and apparatus for medical treatment and more particularly to microcatheters and related methods for injecting therapeutic or diagnostic substances into the bodies of human or animal subjects.

BACKGROUND

In a variety of situations is desirable to deliver therapeutic or diagnostic substances (e.g., drugs, biologics, cells, genes, fillers, tissue adhesives, etc.), articles (e.g., implants, beads, coils, pellets, etc.) or devices (e.g., guidewires, sensors, etc.) to specific locations within body of a human or animal subject. Examples of target locations to which substances, articles and/or devices may be delivered include: organs, body lumens, myocardial tissue, infarcted or necrotic tissue, brain tissue, skeletal muscle, nerves, blood vessel walls, tumors and other normal or pathological tissues. Also, in some instances, it may be desirable to advance a catheter into or adjacent to a previously implanted device (e.g., a refillable drug delivery reservoir, a prosthetic device, a fluid filled implant, etc.) to deliver a substance (e.g., a refill quantity of a drug or fluid, a lubricant, a filler material, etc.), article (e.g., a small battery or other item) or some ancillary apparatus (e.g., a power supply wire, etc.) to that previously implanted device.

Some catheters and implantable substance delivery devices (e.g., drug eluting stents) have been employed to indirectly deliver drugs or substances to specific target locations within the body by releasing the drug within the lumen of a nearby blood vessel and allowing the drug to diffuse through the blood vessel wall or distribute through downstream capillaries, to the desired target location.

The prior art has also included catheter devices that may be used for delivering substances or apparatus directly into interstitial target locations by guided advancement of a penetrating catheter into the lumen of a blood vessel and subsequently advancing a penetrator such as a hollow needle from the catheter, into or through the wall of the blood vessel in which the catheter is positioned and through any intervening tissue to the target site. The desired substance or apparatus may then be delivered.

Particular interest has developed in methods for controlled or targeted delivery of substances such as drugs (e.g., chemotherapeutic agents), gene therapy compositions (e.g., plasmids, viral vectors, genetically modified cells, naked DNA), biological factors (e.g., angiogenic factors, nerve growth factors, other cell growth factors, other proteins), monoclonal antibodies, or specific cell types (e.g., stem cells or other progenator cells, pancreatic islet cells, dopamine secreting neurons, endothelial cells, myocardial cells, other myocytes, etc) into interstitial target locations for the purpose of treating diseases such as myocardial ischemia, solid tumor types of cancer, parkansonism, diabetes, etc. Specifically, in the treatment of myocardial ischemia, research has indicated that introduction of certain angiogenic substances into ischemic areas of myocardium may result in therapeutic angiogenesis in patients who suffer from clinically significant coronary artery disease. Generally speaking, the term "angiogenesis" refers to the creation of new capillaries and/or blood vessels within the parenchyma of an organ, within a tumor or within an area of tissue (e.g., myocardium). Angiogenesis is believed to occur as a multistep process in which endothelial cells focally degrade and invade through their own basement membrane, migrate through interstitial stroma toward an angiogenic stimulus, proliferate proximal to the migrating tip, organize into blood vessels, and reattach to newly synthesized basement membrane. The term "therapeutic angiogenesis" generally refers to the administration of angiogenic substances or treatments to promote creation of new blood vessels or capillaries in tissues that previously lacked sufficient blood flow.

Various approaches have heretofore been used for delivery of angiogenic substances into the myocardium. One approach is the use a tissue penetrating device, such as a laser, to create penetration tracts or transmyocardial (TMR) channels which extend from either the epicardial (outer) surface or endocardial (inner) surface of the heart into the myocardium, and to then inject quantities of angiogenic substances into those TMR channels. Examples of this approach are described in U.S. Pat. No. 5,925,012 (Murphy-Chutorian, et al.), U.S. Pat. No. 5,999,678 (Murphy-Chutorian, et al.) And U.S. Pat. No. 6,106,520 (Laufer, et al.).

There remains a need in the art for the development of new apparatus and methods for delivering substances or apparatus to specific target sites within tissues, tumors or organs of the body with minimal trauma to the tissues and optimum control as to the precise location(s) at which the substances or apparatus are introduced.

SUMMARY OF THE INVENTION

In accordance with the present invention there is provided a delivery catheter device that is useable to deliver a substance, article or device to a location within the body of human or animal subject. Such delivery catheter device generally comprises i) a catheter body having a side wall, a lumen and a distal end, ii) a tissue penetrating distal tip member on the distal end of the catheter body and iii) one or more delivery aperture(s) such that a substance, article or device bay be delivered through the lumen of the catheter body and out of the delivery aperture(s). The tissue penetrating distal tip member allows this delivery catheter device to be advanced (e.g., pushed) through tissue to a desired location prior to delivery of the substance, article or device. In some embodiments, the tissue penetrating distal tip member may be substantially formed of a metal, such as platinum and at least a distal portion of the catheter body may be formed of polymeric material or metal. In some embodiments, such as where the tissue penetrating distal tip member is formed of platinum and at least the distal portion of the catheter body is formed of polymeric material, the tissue penetrating distal tip member may be radiographically visible thereby enabling the operator to discern the in situ position of the distal tip on the catheter device using fluoroscopy or other radiographic imaging techniques. In some embodiments, the distal tip member may be closed and the delivery aperture(s) may be formed in the sidewall of the catheter body. In other embodiments a delivery opening (e.g., a longitudinal bore) may be formed in the distal tip member (with or without other delivery aperture(s) in the sidewall of the catheter body), thereby allowing the desired substance, article or device to be delivered through the distal tip member.

Further in accordance with the present invention, there is provided a method for delivering a substance, article or device to a target location within the body of a human or animal subject. In general, this method comprises the steps of: (A) providing a tissue penetrating catheter that is positionable in a body lumen within the subject's body and has a tissue penetrating member that is advanceable to a first location outside of the body lumen, (B) providing a delivery catheter has a tissue penetrating distal tip and is advanceable through or over the tissue penetrating member of the tissue penetrating catheter device, (C) positioning the tissue penetrating catheter in a body lumen within the subject's body, (D) advancing the tissue penetrating member from the tissue penetrating catheter to a first location outside of the body lumen in which the tissue penetrating catheter is positioned, (E) advancing the delivery catheter through or over the tissue penetrating member such that the tissue penetrating distal tip of the delivery catheter penetrates further through tissue to or through the target location and (F) using the delivery catheter to deliver a substance, article or device to the target location. The tissue penetrating catheter may comprise any of the tissue penetrating catheters described in U.S. Pat. No. 5,830,222 (Makower), U.S. Pat. No. 6,068,638 (Makower), U.S. Pat. No. 6,159,225 (Makower), U.S. Pat. No. 6,190,353 (Makower, et al.), U.S. Pat. No. 6,283,951 (Flaherty, et al.), U.S. Pat. No. 6,375,615 (Flaherty, et al.), U.S. Pat. No. 6,508,824 (Flaherty, et al.), U.S. Pat. No. 6,544,230 (Flaherty, et al.), U.S. Pat. No. 6,579,311 (Makower), U.S. Pat. No. 6,602,241 (Makower, et al.), U.S. Pat. No. 6,655,386 (Makower, et al.), U.S. Pat. No. 6,660,024 (Flaherty, et al.), U.S. Pat. No. 6,685,648 (Flaherty, et al.), U.S. Pat. No. 6,709,444 (Makower), U.S. Pat. No. 6,726,677 (Flaherty, et al.) and U.S. Pat. No. 6,746,464 (Makower), the entire disclosure of each such United States patent being expressly incorporated herein by reference. Also, commercial examples of such tissue penetrating catheters are the Pioneer™ catheter (Medtronic Vascular, Santa Rosa, Calif.) and the Outback™ catheter (LuMend, Inc., Redwood City, Calif.) as well as other devices used for endocardial approaches.

Further aspects, details and embodiments of the present invention will be understood by those of skill in the art upon reading the following detailed description of the invention and the accompanying drawings.

BRIEF DESCRIPTION OF THE DRAWINGS

FIG. 2A is an enlarged view of portion 2A of FIG. 2.

DETAILED DESCRIPTION

The following detailed description, the accompanying drawings are intended to describe some, but not necessarily all, examples or embodiments of the invention. The contents of this detailed description and accompanying drawings do not limit the scope of the invention in any way.

Delivery Catheter Device

Figures 1, 1A:
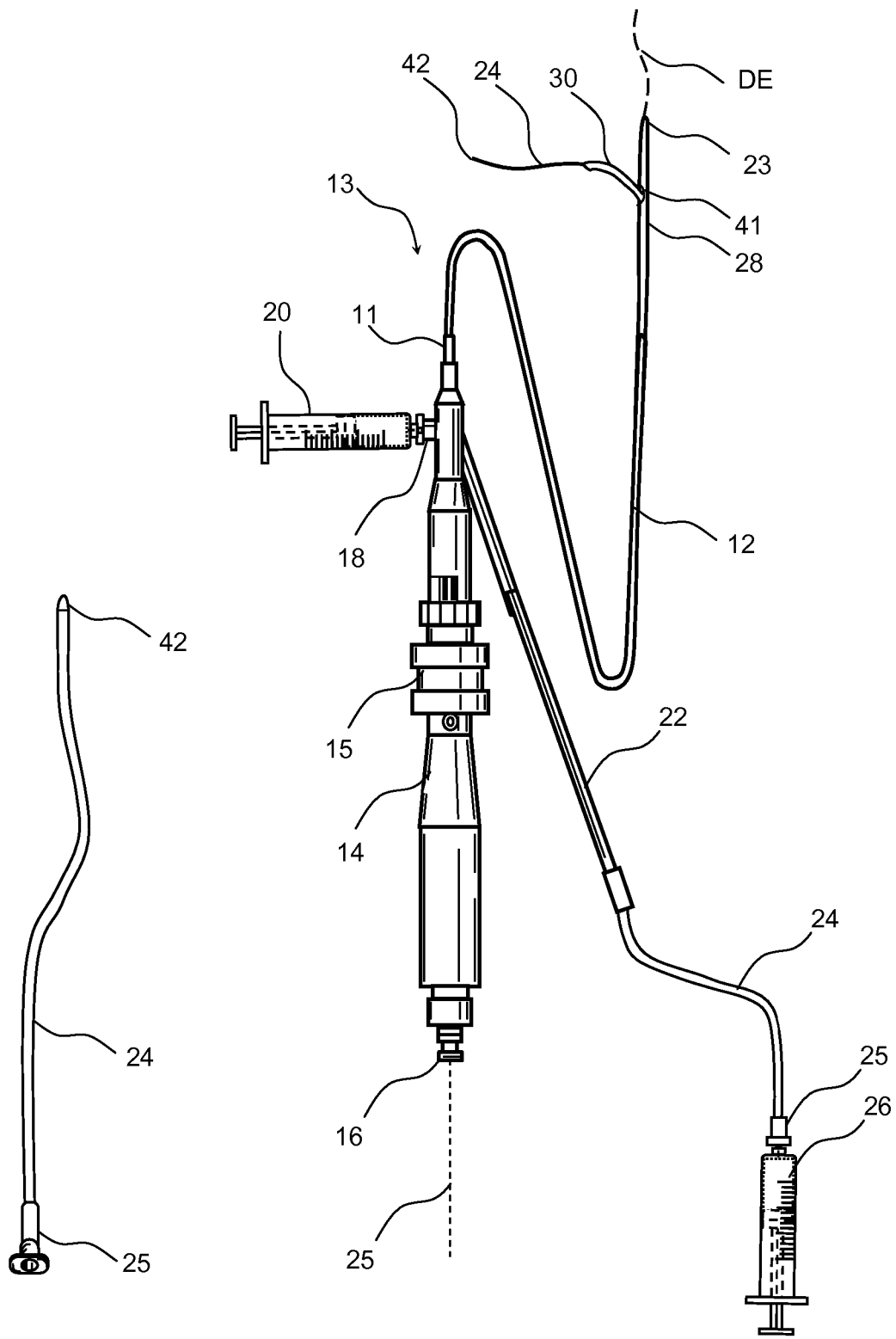
FIG. 1 is a perspective view of a delivery catheter of the present invention having a tissue-penetrating distal tip.
FIG. 1A is a side view of one embodiment of a system of the present invention comprising a tissue penetrating catheter having a hollow tissue penetrating member through which the delivery catheter of FIG. 1 may be inserted.

FIG. 1 shows a delivery catheter 10 of the present invention comprising a catheter body 24, a Luer connector 25 on the distal end of the catheter body 24 and a tissue penetrating distal tip member 42 on the distal end of the catheter body 24. As described fully hereblow, delivery aperture(s) are formed in the catheter body 24 and/or distal tip member 42, but such delivery apertures are not seen in the view of FIG. 1. This delivery catheter 10 bay be of any suitable length and diameter. In a number of embodiments, the delivery catheter 10 may comprise a microcatheter wherein the catheter body 12 and distal tip member 42 are no more than 016 inch in outer diameter so as to be advanceable through the lumen of a needle or hypotube. Any suitable materials may be used to form the delivery catheter device 10. In some embodiments, the catheter body may be formed substantially of polymeric material (e.g., polyether block amides (Pebax), Nylon, polyethylene, polyimides, polysulfones, polyetherimide (ULTEM), polyamide-imides (Torlon), etc. In some embodiments, all or part of the catheter body 12 may be formed substantially of metal, such as stainless steel hypotube, thereby imparting additional column strength to the catheter body 12 to facilitate pushing of the delivery catheter device 10 through tissue. The tissue penetrating distal tip member 42 may also be formed of any suitable materials, including a variety or metals or polymeric materials. In some embodiments, the tissue penetrating distal tip member 42 may be formed substantially of a dense, radiopaque metal such as platinum, iridium, tantalum, tungsten or gold. Examples of some but not all ways in which the catheter body 12 and distal tip member 42 may be constructed are shown in FIGS. 4A-4G.

Figure 4:
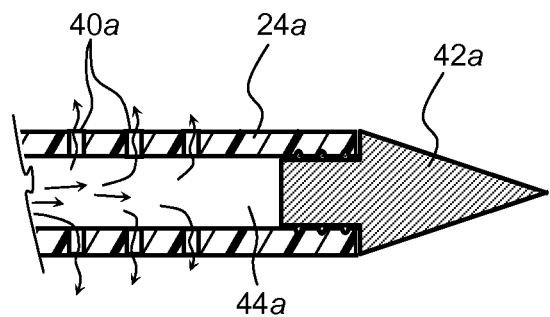
FIG. 4A is a longitudinal sectional view of a distal portion of a delivery catheter of the present invention having an internally mounted distal tip member that is substantially conical.
FIG. 4B is a longitudinal sectional view of a distal portion of a delivery catheter of the present invention having an internally mounted distal tip member that is substantially conical and emits energy.
FIG. 4C is a longitudinal sectional view of a distal portion of a delivery catheter of the present invention having an internally mounted distal tip member having a that is substantially tapered.
FIG. 4D is a longitudinal sectional view of a distal portion of a delivery catheter of the present invention having an internally mounted distal tip member that is substantially conical with an outflow opening formed therein.
FIG. 4E is a longitudinal sectional view of a distal portion of a delivery catheter of the present invention having an externally mounted distal tip member that is substantially conical with an outflow opening formed therein.
FIG. 4F is a perspective view of a distal portion of a delivery catheter of the present invention having a pointed distal tip member and side apertures formed in the catheter body.
FIG. 4G is a longitudinal sectional view of a distal portion of the delivery catheter of FIG. 4F.
Figure 4:
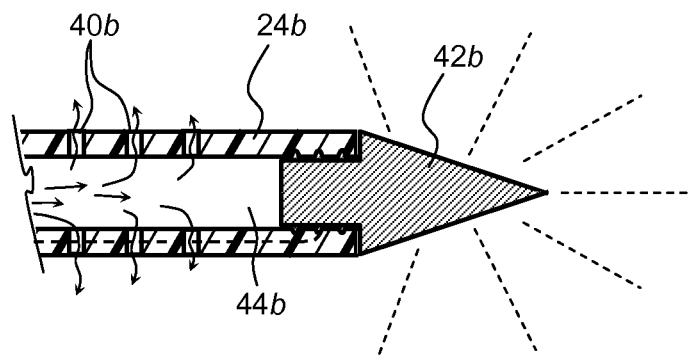
Figure 4:
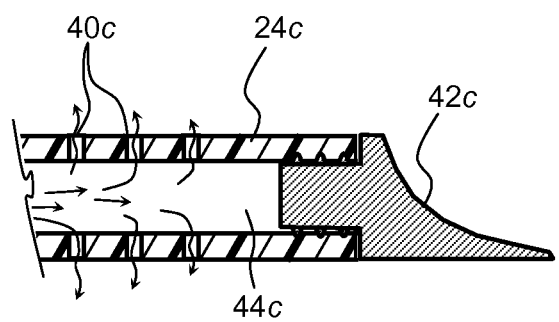
Figure 4:
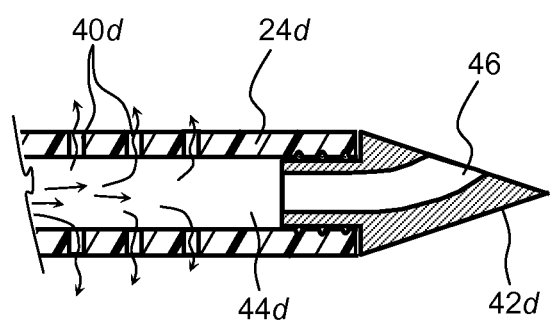
Figure 4:
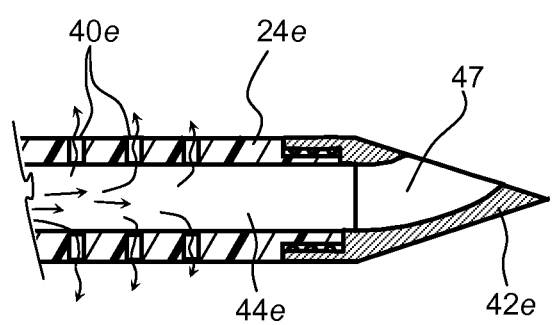

In the embodiment of FIG. 4A, the tissue penetrating distal tip member 42a comprises a solid, pointed, conical metal tip the proximal end of which is inserted into the distal end of the catheter body lumen 44a and secured to the surrounding side wall of the catheter body 24a by frictional engagement, undercut construction, adhesive, or any other suitable means. Delivery apertures 40a are formed in the side wall of the catheter body 24a such that a flowable substance may be infused through lumen 44a and out of delivery apertures 40a.

The embodiment of FIG. 4B is similar to that of FIG. 4A, but includes a distal tip member 42b which is energized such that it may act as an electrode, sensor, cautery, etc. In the showing of FIG. 4B, the distal tip member 42b comprises a solid, pointed, conical metal tip the proximal end of which is inserted into the distal end of the catheter body lumen 44a and secured to the surrounding side wall of the catheter body 24a by frictional engagement, undercut construction, adhesive, or any other suitable means. Delivery apertures 40b are formed in the side wall of the catheter body 24a such that a flowable substance may be infused through lumen 44b and out of delivery apertures 40b. Connector wire(s) 45 extend through the catheter body 24b to send current and/or signals to/from the distal tip member 42b. In some embodiments, the distal tip member may be constructed to act as a monopolar or bipolar electrode which, when energized, will warm to a temperature that facilitates ease of advancement through tissue.

In the embodiment of FIG. 4C, the tissue penetrating distal tip member 42c comprises a solid metal tip having a beveled distal face. The proximal end of this distal tip member 42c is inserted into the distal end of the catheter body lumen 44c and secured to the surrounding side wall of the catheter body 24a by frictional engagement, undercut construction, adhesive, or any other suitable means. Delivery apertures 40c are formed in the side wall of the catheter body 24c such that a flowable substance may be infused through lumen 44c and out of delivery apertures 40c.

FIG. 4D shows an embodiment of a delivery catheter wherein the distal tip member 42d comprises a pointed, conical metal tip having a hollow bore 46 extending therethrough such that a substance, apparatus or device may be delivered though the catheter body lumen 44d, through bore 46 and out of the distal end of the delivery catheter device. The proximal end of this distal tip member 42d is inserted into the distal end of the catheter body lumen 44d and secured to the surrounding side wall of the catheter body 24d by frictional engagement, undercut construction, adhesive, or any other suitable means. Since the distal tip member 42d of this embodiment includes a bore 46, it may not be necessary or desirable to form additional delivery apertures in the side wall of the catheter body 24d. However, in the example of FIG. 4D, optional delivery apertures 40d are formed in the side wall of the catheter body 24a such that a flowable substance may be infused through lumen 44b and out of delivery apertures 40d as well as through bore 46.

FIG. 4E shows another embodiment where the distal tip member 42e has a hollow bore 47 extending therethrough, but in this embodiment the proximal end of the distal tip member 42e is secured to the outer surface of the catheter body 24e, thereby allowing the diameter of the bore 48e to be substantially the same as the diameter of the catheter body lumen 44e. The provision of a distal tip bore 47 that is the same diameter as the lumen 44e eliminates any step down or shoulder within the lumen and may facilitate infusion of viscous substances or the delivery of solid articles or devices. As shown, an area of reduced outer diameter may be created on the distal end of the catheter body 24e such that the proximal end of the distal tip member 42e may be received about and secured to that area of reduced diameter by frictional engagement, undercut construction, adhesive, or any other suitable means. In this construction, the outer diameter of the proximal end of the distal tip member 42e may also be substantially the same as the outer diameter of the adjacent catheter body, thereby providing a substantially continuous and smooth outer surface. Since the distal tip member 42e of this embodiment includes a bore 47, it may not be necessary or desirable to include and delivery apertures in the side wall of the catheter body 24d. However, in the example of FIG. 4e, optional delivery apertures 40e are formed in the side wall of the catheter body 24e such that a flowable substance may be infused through lumen 44e and out of delivery apertures 40e as well as through bore 46.

Figure 4F:
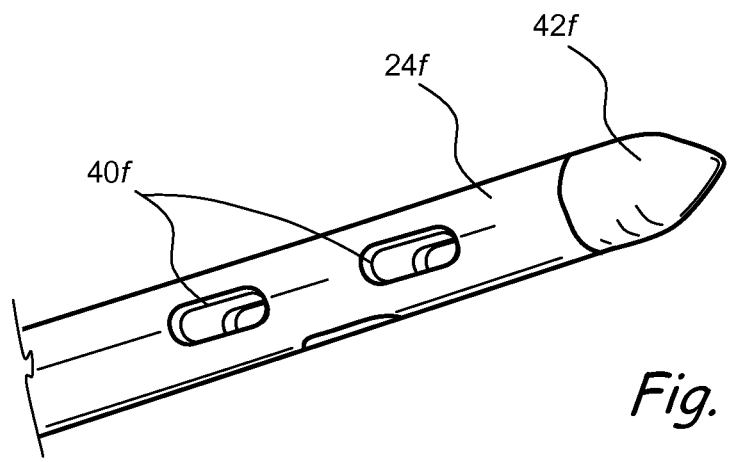
Figure 4G:
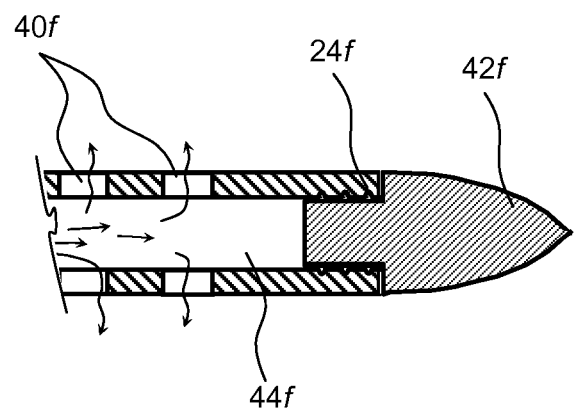

FIGS. 4F and 4G show yet another embodiment of a delivery catheter device wherein the tissue penetrating distal tip member 42f comprises a solid metal member having a radially tapered configuration, as shown. The proximal end of this distal tip member 42f is received within the distal end of the catheter body lumen 44f and secured to the surrounding side wall of the catheter body 24f by frictional engagement, undercut construction, adhesive, or any other suitable means. Longitudinally elongated delivery apertures 40f are formed in the side wall of the catheter body 24f such that a flowable substance may be infused through lumen 44f and out of delivery apertures 40f.

Tissue Penetrating Catheter/Delivery Catheter System

Figure 2:
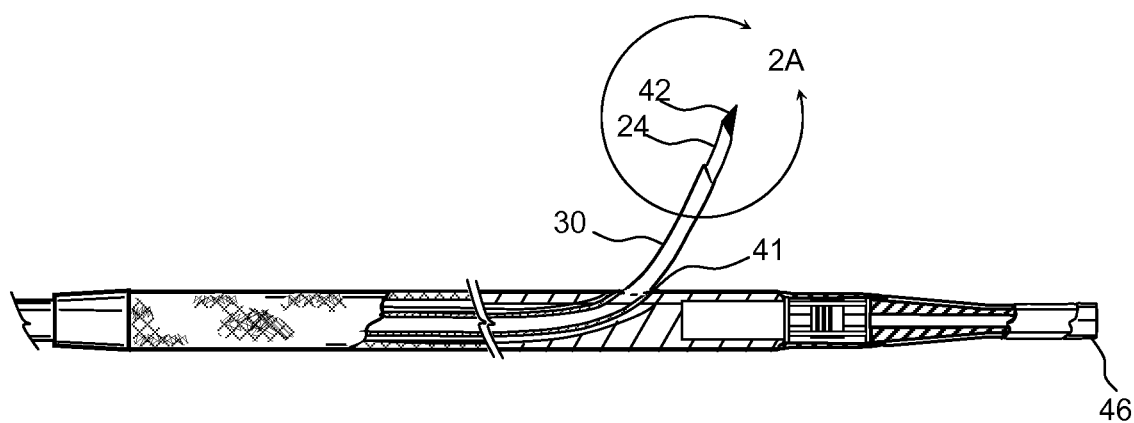
FIG. 2 is an enlarged view of a distal portion of the system of FIG. 1.
Figure 2:
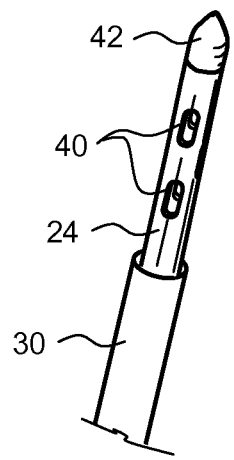

FIGS. 1A, 2 and 2A show a system 13 of the present invention comprising a delivery catheter device 10 as described hereabove in combination with a tissue penetrating catheter device 11.

The tissue penetrating catheter device 11 comprises a catheter body 12 that is positionable within a natural or man-made anatomical lumen (e.g., the lumen of a blood vessel, previously made penetration tract or other lumen or passageway within a human or animal body). A tissue penetrating member 30 is advanceable from the catheter body 12 to a first location outside of the anatomical lumen in which the catheter body 12 is positioned. The delivery catheter device 10 is advanceable through or over the tissue penetrating member 30 such that the tissue penetrating distal tip member 42 of the delivery catheter device 10 will penetrate through further tissue to a second location.

The catheter body 12 of the tissue penetrating catheter device 10 may have a handpiece 14 on its proximal end. As seen in FIG. 2, a side port 41 may be formed in the sidewall of the catheter body 12. The tissue penetrator 30 may be moveable between a retracted position where at least the distal portion of the penetrator 30 is within a curved tubular penetrator housing 40 and an extended position wherein the penetrator 30 extends out of side port 41. The penetrator 30 may comprise a member (e.g., a probe or needle) over which or through which the delivery catheter body 24 may be advanced. In the particular embodiment shown in the drawings, the penetrator 30 comprises a curved needle having a hollow lumen 32 and an open distal end. This penetrator may be formed of nickel-titanium alloy (e.g., Nitinol) or other superelastic or elastic material and may be biased to a curved configuration, as seen in the drawings. A proximal side arm 27 is connected to the proximal end of the penetrator lumen 32. The delivery catheter body 24 is advanceable through the proximal side arm 23 and through the lumen 32 of the penetration member 30. As seen in FIG. 2, after the delivery catheter has emerged out of the distal end of the penetrator 30, the tissue penetrating distal tip member 42 will penetrate through further tissue to a desire location. At that time, the desired substance, article or device may be delivered though one or more delivery apertures 40 formed in the catheter body 24 and/or tip member 42.

A handpiece 14 may be mounted on the proximal end of the tissue penetrating catheter body 12. Such handpiece 14 may comprise a penetrator advancement/retraction knob 15 which may be pushed in the distal direction to advance the penetrator 30 from its retracted position to its extended position and pulled in the proximal direction to retract the penetrator from its extended position to its retracted position. An adjustable stop member 17 limits the extent of distal advancement of the penetrator advancement/retraction knob 15, thereby controlling the length from the side port 28 to the distal tip of the penetrator 30 when the penetrator 30 is fully extended.

A proximal port 16 on the handpiece 14 connects to a lumen 38 that extends longitudinally through the catheter body 12. A tapered distal tip member 39 having a lumen 38 (tip) is mounted on the distal end of the catheter body 12. The distal tip member lumen 38 (tip) is continuous with the lumen 38 of tube 36, such that a continuous lumen 38, 38 (tip) extends from proximal port 16 though the open distal end of distal tip member 39. A guidewire 25 may pass through this lumen 38, 38 (tip) for over-the-wire advancement of the catheter device 10. It will be appreciated that, in some alternative embodiments, the lumen 38 may terminate proximally in a side opening in the catheter body 12, thereby providing a rapid exchange type guidewire lumen.

In the embodiment shown, an infusion port 18 is optionally formed on the handpiece 14 in communication with lumen 38 such that an infusion apparatus 20 (e.g., a syringe, intravenous tube, pump, injector, etc.) may be used to infuse fluid (e.g., saline solution, radiographic contrast medium, etc.) through lumen 38, 38 (tip) and out of the open distal end of the tip member 46. A valve (e.g., a Tuohi-Borst valve) may be provided on proximal port 16 to secure a guidewire 25 when desired and/or to form a fluid tight seat at proximal port 16 when fluid is being infused through infusion port 18.

Methods of Use

Figure 3:
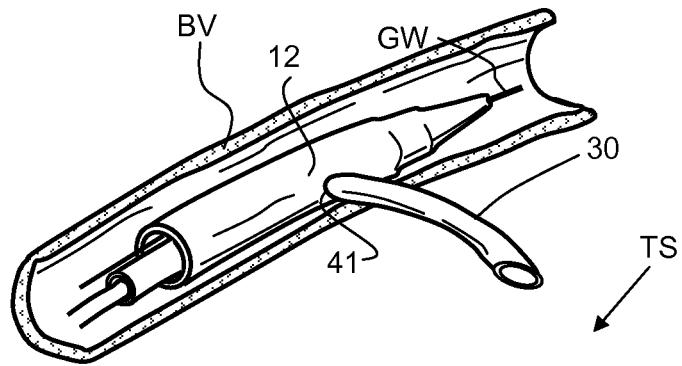
FIGS. 3A-3C are schematic diagrams showing steps in a method wherein the system of FIG. 1 is used to deliver of a substance to a desired target location within the body of a human or animal subject.
Figure 3:
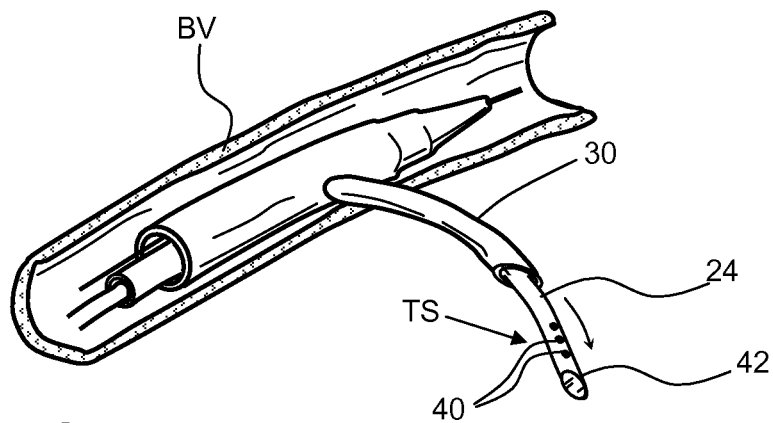
Figure 3:
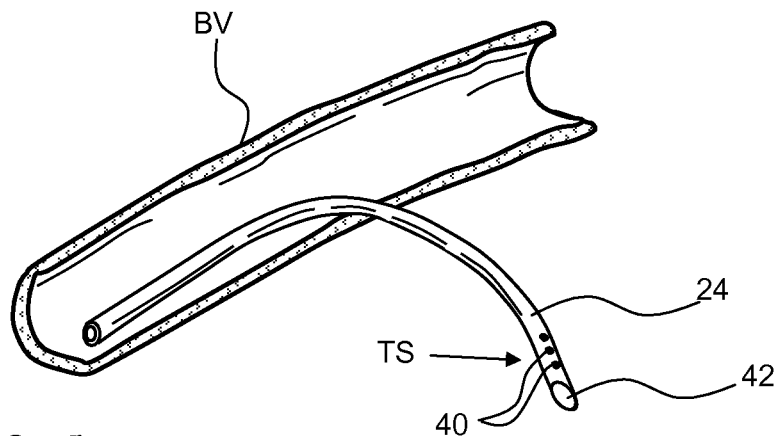

A non-limiting example of a method by which the above-described system may be used is shown in FIGS. 3A-3C.

With reference to FIG. 3A, a guide wire GW is percutaneously inserted into the vasculature and advanced into a blood vessel BV that is located adjacent to an interstitial target site TS to which a substance is to be delivered. Thereafter, the penetrating catheter body 12 is advanced over the guidewire GW and into the blood vessel BV. The penetrating catheter body 12 is positioned and rotationally oriented within the lumen of the blood vessel BV such that the penetrator outlet aperture 41 is radially directed toward (e.g., "aimed at") the target site TS and/or the expected trajectory of penetrator advancement is such that subsequent advancement of the penetrator 30 will cause the penetrator 30 to move in the direction of the target site TS. To facilitate any needed adjustment of the rotational orientation of the catheter body 12 within the blood vessel BV lumen, the penetrating catheter device 13 may incorporate imaging apparatus and/or one or more markers or indicator devices for indicating the current rotational orientation of the catheter body 12 and/or the projected path on which the penetrator will subsequently advance. Examples of such imaging apparatus and/or one or more markers or indicator devices and their methods of use are described in U.S. Pat. No. 5,830,222 (Makower), U.S. Pat. No. 6,068,638 (Makower), U.S. Pat. No. 6,159,225 (Makower), U.S. Pat. No. 6,190,353 (Makower, et al.), U.S. Pat. No. 6,283,951 (Flaherty, et al.), U.S. Pat. No. 6,375,615 (Flaherty, et al.), U.S. Pat. No. 6,508,824 (Flaherty, et al.), U.S. Pat. No. 6,544,230 (Flaherty, et al.), U.S. Pat. No. 6,579,311 (Makower), U.S. Pat. No. 6,602,241 (Makower, et al.), U.S. Pat. No. 6,655,386 (Makower, et al.), U.S. Pat. No. 6,660,024 (Flaherty, et al.), U.S. Pat. No. 6,685,648 (Flaherty, et al.), U.S. Pat. No. 6,709,444 (Makower), U.S. Pat. No. 6,726,677 (Flaherty, et al.) and U.S. Pat. No. 6,746,464 (Makower), the entire disclosures of which are expressly incorporated herein by reference. After any needed adjustment of the position or rotational orientation of the tissue penetrating catheter body 12 has been made, the penetrator 30 is advanced out of aperture 41, through the wall of the blood vessel BV and into adjacent tissue such that the distal end of the penetrator 30 advances to a first location that is generally between the blood vessel BV and the target site TS.

As seen in FIG. 3B, the delivery catheter body 24 is then advanced through the lumen of the penetrator 30 such that the tissue penetrating distal tip member 42 penetrates from the distal end of the penetrator 30, through intervening tissue, and through the target site TS such that delivery apertures 40 formed in the sidewall of the delivery catheter body 24 are positioned within the target site TS. The desired substance is then infused through the lumen of the delivery catheter body 24 and out of delivery apertures 40 to the target site. In the particular example shown, the tissue penetrating distal tip member 42 is closed and, thus, the distal tip member 42 is advanced through and slightly beyond the target site TS such that the delivery apertures are within the target site. It is to be appreciated, however, that in other application of the invention, such as those using a delivery catheter 10 that has an opening is formed in the distal tip member 42 (such as bore 46 in FIG. 4D or bore 48 in FIG. 4E), the distal tip member 42 may be advanced to a position that is within the target site TS such that a substance delivered out of the opening in the distal tip member 42 will enter the target site. It will be further appreciated that in some applications the target site TS may be a relatively small or focal site while in others the target site may be relatively large or diffuse. In cases where the target site is relatively large or diffuse, substance may be infused through the delivery catheter continuously or in boluses as the delivery catheter is advanced or withdrawn, thereby depositing the substance over a greater area than is the delivery catheter 10 were maintained in a stationary position during the substance infusion(s). Also, in embodiments where the penetrator 30 is curved, as seen in FIGS. 3A-3B, the delivery catheter body 24 may be advanced from the penetrator 30 a plurality of times and used to administer a plurality of substance infusions, with changes in the positioning or degree of advancement of the penetrator 30 between such advancements of the delivery catheter 10 and infusions of substance. This allows for deposition of substance over a angular or fan shaped area. Examples of these techniques are provided in copending U.S. Pat. No. 6,602,241, of which this application is a continuation-in-part and which is expressly incorporated herein by reference.

Examples of the types of substances that may be delivered through the delivery catheters 10 of the present invention include but are not limited to therapeutic, diagnostic and cosmetic substances, including: contrast agents or other agents that provide an enhanced image of the target site, traceable substances that may be used to determine the rate at which the substance distributes away from or is otherwise inactivated at the target site or other pharmacokinetic or biodistributive parameters or variables, drugs, proteins, cells (e.g., stem cells, nerve cells, progenator cells, myoblasts, myocytes, secretory cells, pancreatic islet cells, dopamine secreting cells, endothelial cells, hepatocytes, cloned cells, cells grown in cell culture, genetically modified cells, and combinations thereof), angiogenic substances (e.g., vascular endothelial growth factor (VEGF), fibroblast growth factors (FGF), epidermal growth factor (EGF), platelet-derived growth factor (PDGF), hepatocyte growth factor (HGF) or scatter factor, heparin combined with an adenosine receptor agonist, nerve cell growth factor (NGF), and combinations thereof), other agents that increase vascularity of an ischemic target site, myogenic substances, neurogenic substances, genes, gene therapy compositions, genetic material in combination vectors (e.g., viruses), stem cells of a type that will mature in situ into a type of cell that is currently deficient, substances that promote the growth of myocytes in tissue that is necrotic or characterized by a lack of living myocytes, secretory cells that secrete a substance (e.g., dopamine, insulin, a particular neurotransmitter) that is deficient, tep F comprises insulin secreting cells, glial cell line-derived neurotropic factor (GDNF), nerve growth factor, neuro-immunophilin ligand, poly ADP-Ribose polymerase, bulking agents or fillers, and combinations thereof.

In applications of the invention where an article is to be delivered to the target site, it will be appreciated that in some cases such article may be introduced directly through the lumen 32 of the penetrator 30 and in other cases a tube or other delivery device may be advanced through the penetrator 30 and used to deliver the desire article. Examples of the types of articles that may be delivered include but are not limited to; substance eluting implants, radioactive implants, embolic members, markers, radiopaque markers.

In applications of the invention where a device is to be delivered to the target site, it will be appreciated that in some cases such device may be introduced directly through the lumen 32 of the penetrator 30 and in other cases a delivery device (e.g., a guidewire or catheter) may initially be advanced through the lumen 32 of the penetrator 30 and second device (e.g., a working device) may then be delivered to the target location by way of that delivery device. Examples of the types of articles that may be delivered include but are not limited to; catheters, cannulae, guidewires, wires, electrodes, sensors, microreservoirs, implantable devices, substance eluting or delivering devices, etc.

It is to be further appreciated that the invention has been described hereabove with reference to certain examples or embodiments of the invention but that various additions, deletions, alterations and modifications may be made to those examples and embodiments without departing from the intended spirit and scope of the invention. For example, any element or attribute of one embodiment or example may be incorporated into or used with another embodiment or example, unless to do so would render the embodiment or example unsuitable for its intended use. Also, where the steps of a method or process are described, listed or claimed in a particular order, such steps may be performed in any other order unless to do so would render the embodiment or example not novel, obvious to a person of ordinary skill in the relevant art or unsuitable for its intended use. All reasonable additions, deletions, modifications and alterations are to be considered equivalents of the described examples and embodiments and are to be included within the scope of the following claims.

What is claimed is:

1. A system for delivering a substance to a location within the body of human or animal subject, comprising:
    A) a tissue penetrating catheter device comprising:
        a catheter body that is positionable within a body lumen of the subject; and
        a tissue penetrating member having a lumen, said tissue penetrating member being advanceable, while the catheter body is positioned within a body lumen, from the catheter to a first location outside of that body lumen; and
    B) a substance delivery catheter device that is advanceable through the lumen of the tissue penetrating member, said substance delivery catheter device comprising:
        a substance delivery catheter body comprising a flexible microcatheter that is advanceable through the lumen of the tissue penetrating member, said catheter body having a side wall, a lumen and a distal end;
        a closed, tissue penetrating distal tip member on the distal end of the substance delivery catheter body; the tissue penetrating distal tip member being radiographically distinguishable from the substance delivery catheter body; and
        at least one aperture formed in the side wall of the substance delivery catheter body such that substance delivered through the lumen of the substance delivery catheter will flow out of said at least one aperture.

2. A system according to claim 1 wherein the tissue penetrating distal tip member is formed substantially of radiopaque material.

3. A system according to claim 1 wherein the tissue penetrating distal tip member is substantially formed of metal.

4. A system according to claim 3 wherein the catheter body is formed substantially of polymeric material.

5. A system according to claim 1 wherein at least a distal portion of the catheter body is formed of a first metal and the tissue penetrating distal tip member is formed of a second metal.

6. A system according to claim 5 wherein at least a distal portion of the catheter body is formed of a metal selected from steel and nickel-titanium alloy and the tissue penetrating distal tip member is formed substantially of platinum.

7. A system according to claim 1 wherein the tissue penetrating distal tip member comprises metal and additionally functions as an electrode.

8. A system according to claim 1 wherein substance from the lumen of the catheter body does not flow through the tissue penetrating distal tip member.

9. A system according to claim 8 wherein the tissue penetrating distal tip member has an opening through which substance from the lumen of the catheter body may flow through the tissue penetrating distal tip member.

10. A system according to claim 1 wherein the tissue penetrating member of the tissue penetrating catheter comprises a needle having a hollow lumen and wherein the substance delivery catheter device is advanceable though the lumen of the tissue penetrating member.

11. A system according to claim 10 wherein the tissue penetrating catheter device comprises apparatus that indicates the rotational orientation of the tissue penetrating catheter device within the body lumen relative to the target location such that the operator may adjust the rotational orientation of the tissue penetrating catheter device within the body lumen as needed to substantially ensure that subsequent advancement of the tissue penetrating member will cause the tissue penetrating member to travel to the desired first location rather than some other location.

12. A system according to claim 10 wherein the tissue penetrating catheter device comprises apparatus that indicates the path on which the tissue penetrating member will subsequently advance such that the operator may adjust the rotational orientation and position of the tissue penetrating catheter device within the body lumen as needed to substantially ensure that subsequent advancement of the tissue penetrating member will cause the tissue penetrating member to travel to the desired first location rather than some other location.

* * * * *